(12) United States Patent
Tajima et al.

(10) Patent No.: US 7,767,297 B2
(45) Date of Patent: Aug. 3, 2010

(54) FIBER, FIBER ASSEMBLY, AND FIBER PRODUCING METHOD

(75) Inventors: Takeharu Tajima, Sodegaura (JP); Nobuo Kusamoto, Sumida-ku (JP)

(73) Assignee: Idemitsu Technofine Co., Ltd., Tokyo (JP)

( * ) Notice: Subject to any disclaimer, the term of this patent is extended or adjusted under 35 U.S.C. 154(b) by 0 days.

(21) Appl. No.: 12/181,560

(22) Filed: Jul. 29, 2008

(65) Prior Publication Data

US 2009/0031691 A1 Feb. 5, 2009

(30) Foreign Application Priority Data

Jul. 30, 2007 (JP) ............................. 2007-197274
Apr. 18, 2008 (JP) ............................. 2008-108740

(51) Int. Cl.
*D02G 3/00* (2006.01)

(52) U.S. Cl. ..................... 428/372; 428/373; 428/374; 428/370; 264/465

(58) Field of Classification Search ................. 428/372, 428/364, 365, 370, 373, 374; 264/465
See application file for complete search history.

(56) References Cited

U.S. PATENT DOCUMENTS

| | | | | |
|---|---|---|---|---|
| 3,194,732 A | * | 7/1965 | Neuhauser | 424/447 |
| 3,196,075 A | * | 7/1965 | Neuhauser | 602/48 |
| 3,624,201 A | * | 11/1971 | Balassa | 424/581 |
| 4,219,544 A | * | 8/1980 | Burg | 424/581 |
| 2005/0246840 A1 | * | 11/2005 | Sano et al. | 8/115.51 |
| 2007/0160674 A1 | * | 7/2007 | Nakahara et al. | 424/489 |
| 2009/0149095 A1 | * | 6/2009 | Sano et al. | 442/59 |

FOREIGN PATENT DOCUMENTS

| | | |
|---|---|---|
| EP | 1703015 A1 | 9/2006 |
| JP | 06-122631 A | 5/1994 |
| JP | 06-192443 | 7/1994 |
| JP | 06-254149 | 9/1994 |
| JP | 02000212093 A * | 8/2000 |
| JP | 2005-194663 | 7/2005 |
| WO | 02-40242 A1 | 5/2002 |

OTHER PUBLICATIONS

European Search Report, EP 08 01 3568, completed Apr. 22, 2010, 1 page.
Feng, Yi, et al., "Mimetics of Eggshell Membrane Protein Fibers by Electrospinning," Macromolecular Rapid Communications, 2004, 25, 1038-1043.
Um, I.C., et al., "Electro-Spinning and Electro-Blowing of Hyaluronic Acid," Biomacromolecules 2004, 5, 1428-1436.

* cited by examiner

*Primary Examiner*—N. Edwards
(74) *Attorney, Agent, or Firm*—Millen, White, Zelano & Branigan, P.C.

(57) ABSTRACT

A fiber containing an eggshell membrane component. The fiber is produced by spinning using a solution containing the eggshell membrane component by employing an electrospinning method. A fiber assembly formed from the fiber obtained by employing the electrospinning method imitates a natural eggshell membrane, whereby sufficient air permeability is exhibited. Since the fiber assembly is also excellent in adherence to skin tissue of a human body and stypticity, the fiber assembly may be preferably used as a wound dressing or a cosmetic sheet.

19 Claims, 8 Drawing Sheets

×1000

×10000

FIBER, FIBER ASSEMBLY, AND FIBER PRODUCING METHOD

BACKGROUND OF THE INVENTION

1. Field of the Invention

The present invention relates to a fiber containing an eggshell membrane component, a fiber assembly, and a fiber producing method.

2. Description of Related Art

It has been known that an eggshell membrane can be effectively used as a wound dressing. It is because the eggshell membrane has cell-producing action of amino acid, adherence to texture due to a network structure thereof, appropriate moisture retention, air permeability and the like, which are suitable for the wound dressing. However, since an extractable eggshell membrane varies in size depending on egg size and is not flattened in shape, adjustment of the extractable eggshell membrane to the shape of a wound portion has been difficult. Accordingly, it has been desired to industrially obtain a sheet-like or a film-like dressing consisting of or containing an eggshell membrane component.

Therefore, a technique in which the eggshell membrane is dissolved in thiopropionic acid and the like to produce a film-like or a sheet-like eggshell membrane has been disclosed (for example, see Document 1: JP-A-06-192443 and Document 2: JP-A-06-254149). Further, a method in which a fiber treatment agent is formed from an eggshell membrane powder so as to produce a fabric has been disclosed (for example, see Document 3: JP-A-2005-194663).

However, the film or the sheet disclosed in Documents 1 and 2 does not have a network structure of a natural eggshell membrane. Also, its moisture retention and air permeability, and adherence to texture are not sufficient for using the film or the sheet as the wound dressing or a cosmetic sheet. Further, the fiber treatment agent disclosed in Document 3 does not have enough quality to imitate a structure of the eggshell membrane and a content of the eggshell membrane cannot be easily raised.

SUMMARY OF THE INVENTION

An object of the present invention is to provide a fiber that imitates an eggshell membrane structure using an eggshell membrane component, a fiber assembly and a fiber producing method.

To resolve the above-described problems, the present invention provides the fiber, the fiber assembly and the fiber producing method as described below.

(1) A fiber containing an eggshell membrane component.
(2) The fiber as described in (1) above further containing polyphenols.
(3) The fiber as described in (2) above where the polyphenols contain catechins.
(4) The fiber as described in (3) above where the catechins contain at least one of epicatechin, epicatechin gallate, epigallocatechin, epigallocatechin gallate and attributes thereof.
(5) The fiber as described in any one of (1) to (4) above further containing polymer molecule.
(6) The fiber as described in any one of (1) to (5) above where a content of the eggshell membrane component is 20 mass % or more.
(7) The fiber as described in any one of (1) to (6) above where a diameter of the fiber is 0.01 μm or more and 3 μm or less.
(8) A fiber assembly produced by assembling the fiber as described in any one of (1) to (7) above.
(9) A method for producing the fiber as described in any one of (1) to (7) above, in which a spinning is performed using a solution containing an eggshell membrane component by employing an electrospinning method.
(10) The method for producing the fiber as described in (9) above, in which the solution containing the eggshell membrane component contains polymer molecule.
(11) The method for producing the fiber as described in (9) or (10) above, in which a fiber having a core/sheath structure is spun by employing the electrospinning method.
(12) The method for producing the fiber as described in (11) above, in which the solution containing the eggshell membrane component is used for forming a core portion and a polymer solution is used for forming a sheath portion.
(13) The method for producing the fiber as described in (11) or (12) above, in which the sheath portion is removed after the core/sheath structure is formed by spinning.
(14) The method for producing the fiber as described in any one of (9) to (13) above, in which a cross-linking process is conducted for the spun fiber.

With this arrangement, the fiber assembly formed from the fiber has substantially the same properties of a natural eggshell membrane since the fiber itself contains the eggshell membrane component. Specifically, the fiber assembly according to the present invention has sufficient moisture retention, air permeability by imitating a network structure of the natural eggshell membrane. Also, since the fiber assembly is excellent in adherence to skin tissue of a human body and stypticity, the fiber assembly may be preferably used as a wound dressing, a cosmetic sheet or the like. Further, since a shape and an area of the fiber assembly are not limited, unfavorable features of the nature eggshell membrane that an extractable eggshell membrane varies in size depending on egg size and is not flattened in shape are eliminated. Furthermore, several effects such as antibacterial, antiviral, antioxidative, deodorant and antiallergic effects may be produced when the fiber contains the polyphenols such as the catechins. Water resistance may be also given to the fiber assembly when the polyphenols form a complex with the eggshell membrane component.

According to the fiber producing method of the present invention, the fiber containing the eggshell membrane can be easily obtained by spinning the solution containing the eggshell membrane component by employing the electropinning method. The fiber assembly can be simultaneously produced with the fiber.

DETAILED DESCRIPTION OF PREFERRED EMBODIMENT(S)

Exemplary embodiments of the present invention will be described below.

1. Fiber and Fiber Assembly

A fiber and a fiber assembly according to the present invention contain an eggshell membrane component. In other words, the fiber itself contains the eggshell membrane component.

Figure 5A:
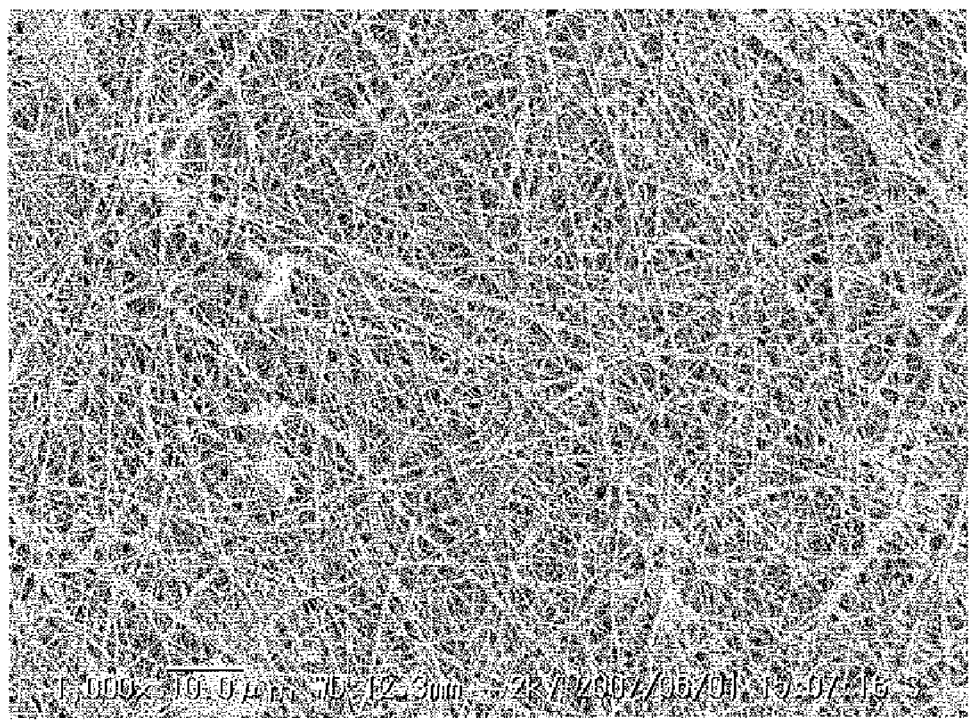
FIG. 5A shows a scanning electron micrograph of a fiber assembly after spinning according to an example 1.
Figure 5B:
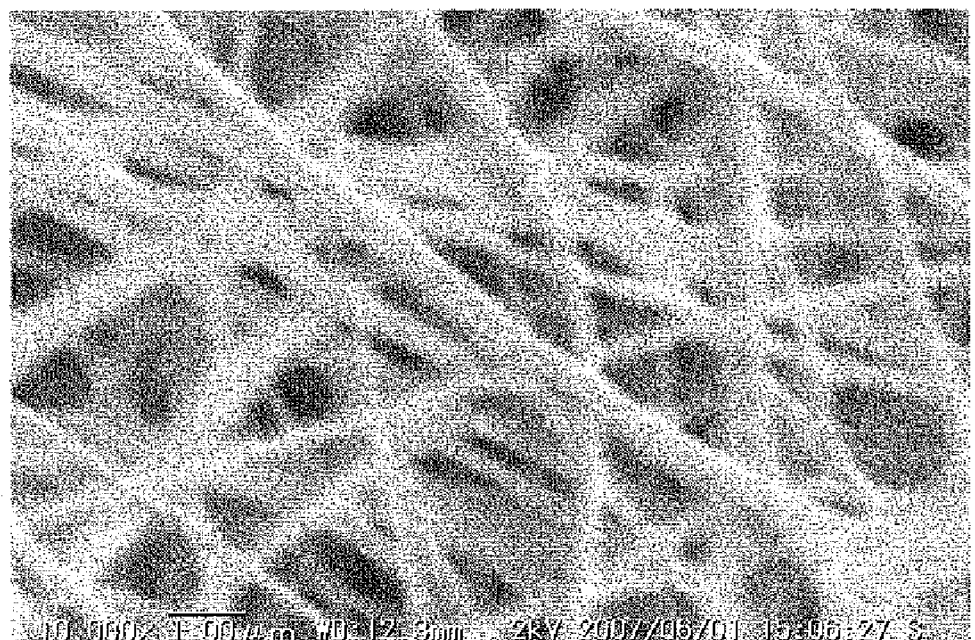
FIG. 5B shows another scanning electron micrograph of the fiber assembly after spinning according to the example 1.

FIGS. 5A and 5B show scanning electron micrographs as examples of the fiber assembly according to the present invention. It should be understood from the micrographs that the fiber assembly imitates a network structure of a natural eggshell membrane. The fiber assembly is used as, for example, a wound dressing.

The fiber and the fiber assembly according to the present invention may additionally contain polyphenols. Examples of the polyphenols include polyhydric phenols such as catechins. The catechins are extracted from a tea leaf, persimmon tannin, bark, cacao bean or the like. Examples of the catechins include epicatechin, epicatechin gallate, epigallocatechin, epigallocatechin gallate and attributes thereof.

The eggshell membrane component is preferably contained in the fiber with a content of 20 mass %, more preferably 50 mass %, most preferably substantially 100 mass %. When the content of the eggshell membrane component is less than 20 mass %, features of the natural eggshell membrane such as cell-producing action and biodegradability are not sufficiently retained.

A fiber diameter according to the present invention is preferably between and including 0.01 μm and 3 μm, more preferably between and including 0.1 μm and 1.8 μm. With such diameter range, a surface area of the fiber assembly can be sufficiently enlarged, and appropriate moisture retention, air permeability and filter effect of the natural eggshell membrane can be exhibited. However, the fiber diameter less than 0.01 μm is not preferable because it may be difficult to produce the fiber with such diameter and the productivity may be lowered.

The above-described fiber and fiber assembly according to the present invention can be produced by employing an electrospinning method (i.e., electrolytic spinning, electrostatic spinning) after pulverizing the eggshell membrane to form a solution.

2. Eggshell Membrane and Eggshell Membrane Solution

The eggshell membrane according to the present invention is preferably obtained from chicken eggs in view of availability, but it is not limited to chicken eggs.

Although the eggshell membrane is relatively easily pulverized and soluble in an organic solvent such as thiopropionic acid, the eggshell membrane is a protein that is inherently insoluble in water. However, a water-soluble hydrolysate or other water-soluble materials of the eggshell membrane component containing a specific quantity of activated thiol group can be obtained after subjecting to an appropriate chemical treatment, enzyme treatment or the like. For example, the soluble eggshell membrane component can be obtained by sequentially or simultaneously conducting a reductive reaction to cleave a protein cross-linking disulfide bond and a hydrolytic reaction to partially cut a high molecular weight protein (see JP-A-2005-194663 for greater detail).

Since the eggshell membrane is solubilized as described above, fiberization (i.e., spinning) using the later-described electrospinning method is easily performed.

With this arrangement, various binders may be dissolved and mixed into the eggshell membrane solution if needed. Commonly-known soluble polymers can be used as the binder, such as polyurethane, silicone, polyvinylidene fluoride, polyacrylonitrile, polymethyl methacrylate, polyvinyl chloride, polyvinylidene chloride, polyethylene, polypropylene, nylon, polyvinyl alcohol, cellulose, polyvinyl acetate, polyethylene oxide, polyethylene imide, polyaniline, polyethylene sulfide, polystyrene, polybutadiene, polyethylene terephthalate, polylactic resin, polyglutamic acid, hyaluronic acid and copolymers thereof. Further examples of the binder include natural polymers such as starch, casein, collagen, nucleic acid, catechin, gelatin, sericin, fibroin, chitin, and chitosan, and sol solutions such as organosilica and organotitanium. By using such binder, the solid fiber and fiber assembly which cannot be obtained from the natural eggshell membrane can be obtained. Also, the above-described various polymers are contained in a fiber-spinning solution, whereby the fiberization (spinning) can be performed more easily using the electrospinning method.

At this time, the above-described polyphenols may be blended with the eggshell membrane solution to obtain the fiber that contains the eggshell membrane component and the polyphenols.

Water is usually used as a solvent, but other solvents that can dissolve the above-described components may be arbitrarily used. Examples of the other solvents include acid, alkali, methanol, ethanol, propanol, isopropanol, acetone, ether, toluene, tetrahydrofuran, cyclohexane, N,N-dimethylformamide, N,N-dimethylacetamide, dimethyl sulfoxide, and chloroform. One of the solvents that can disperse and dissolve the above-described binder uniformly in the eggshell membrane solution may be arbitrarily selected, but more than two kinds of the solvents that are mutually blended may be used in view of spinnability.

If needed, a cross-linking agent (e.g., glutaraldehyde), surfactant, metallic salt, thickner, colorant, preservative or various stabilizers may be blended with the eggshell membrane solution.

When the binder is blended, a blending quantity depends on a purpose such as strength of the finally obtained fiber and fiber assembly.

3. Fiber Producing Device

Next, a fiber producing device according to an exemplary embodiment of the present invention will be described below with reference to the attached drawings.

Figure 1:
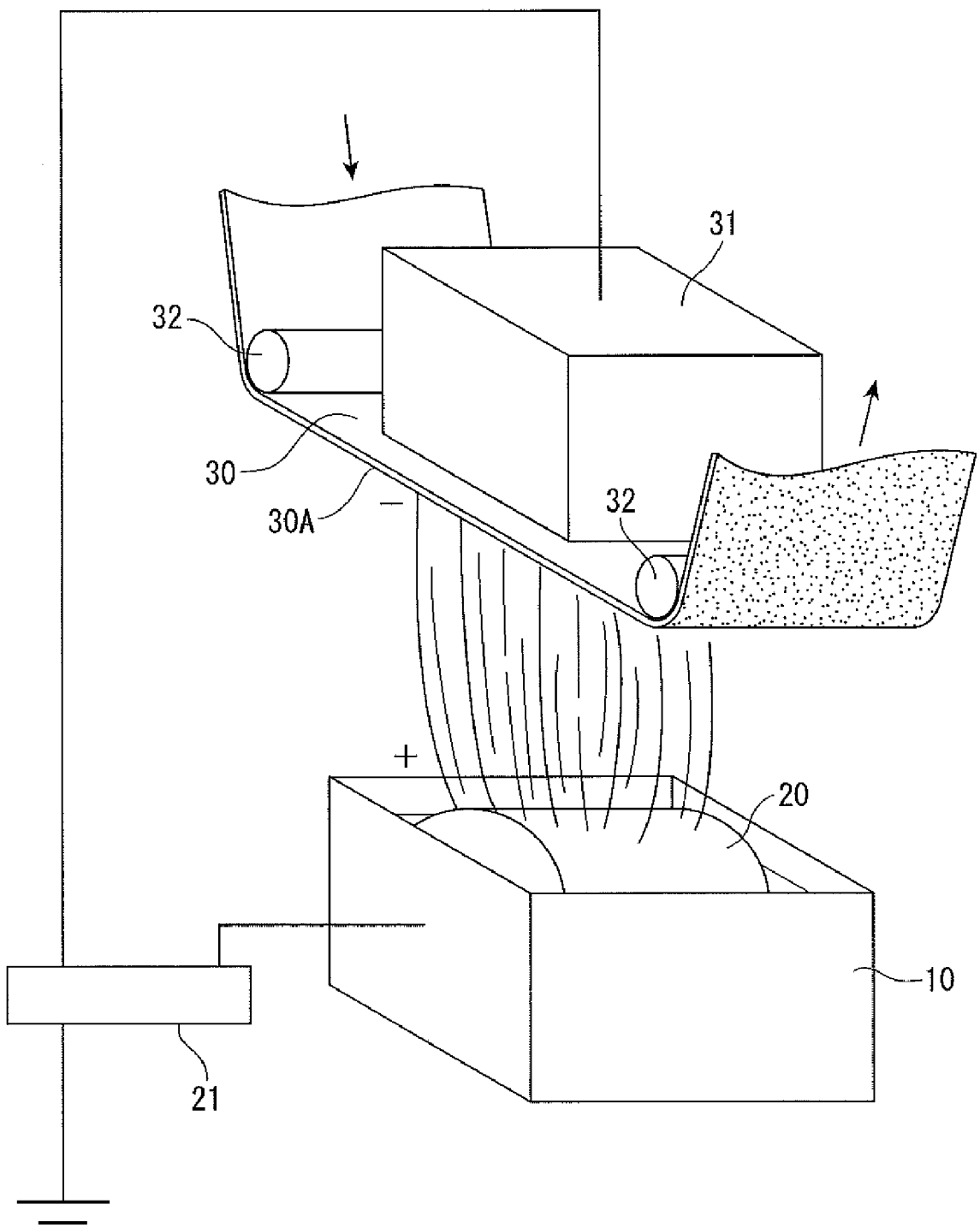
FIG. 1 is a perspective view showing an outline of a producing device for a fiber producing method according to an exemplary embodiment of the present invention.
Figure 2:
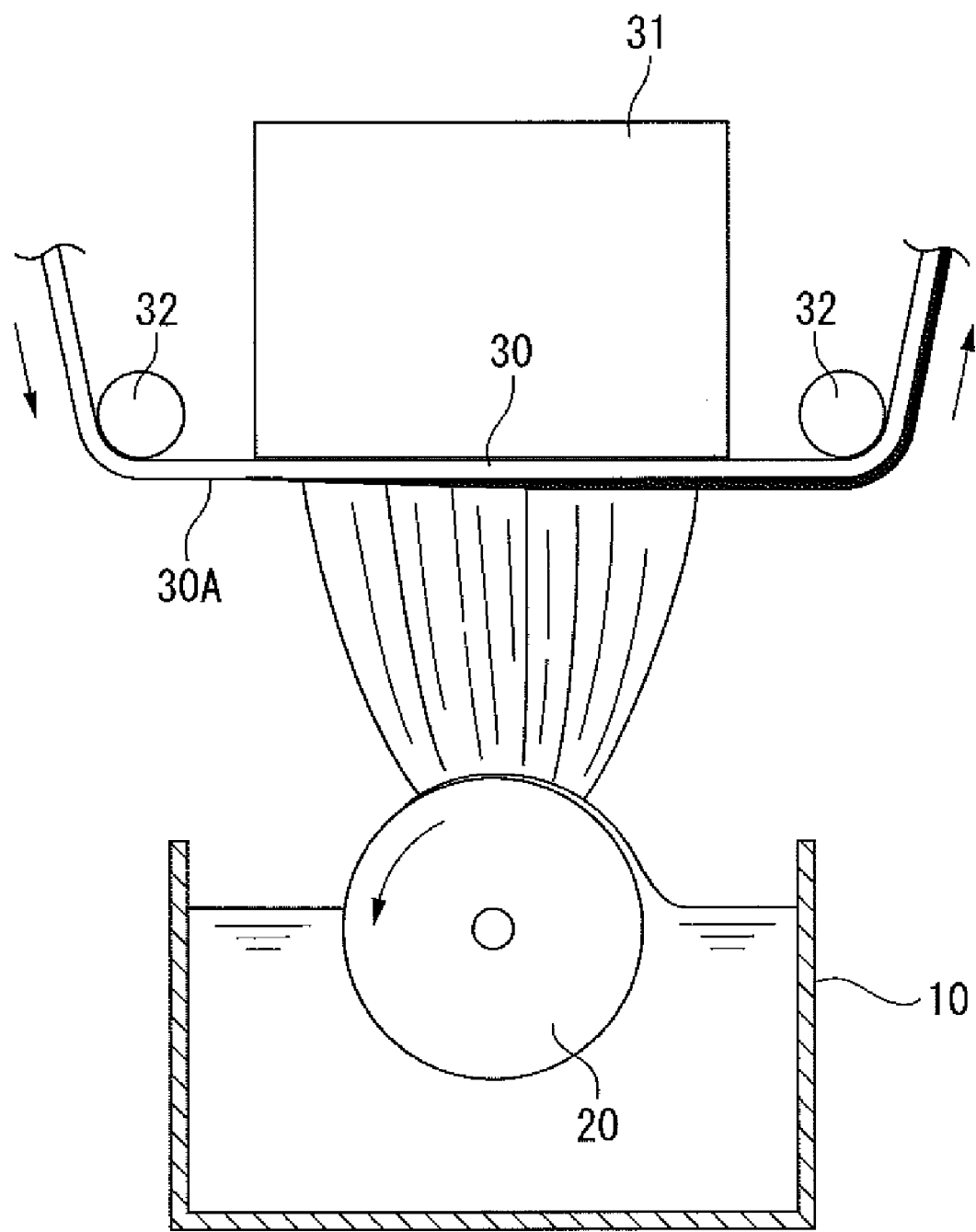
FIG. 2 is a cross sectional view of FIG. 1.

FIG. 1 is a perspective view and FIG. 2 is a cross sectional view showing an outline of the fiber producing device according to the exemplary embodiment of the present invention.

As shown in FIGS. 1 and 2, the electrospinning device is used as the fiber producing device, in which a voltage-applying roller 20 is provided in a solution immersion vessel 10 that is filled with the above-described eggshell membrane solution. The voltage-applying roller 20 is rotatably supported in the solution immersion vessel 10, where at least a circumference of the voltage-applying roller 20 is metallic. A high-voltage generator 21 applies a voltage to the solution immersion vessel 10 which is connected to the high-voltage generator 21. Accordingly, the eggshell membrane solution is positively charged and charges are concentrated on the voltage-applying roller 20. The voltage-applying roller 20 is connected to a rotary driving mechanism (not shown).

An accumulation conveyor 30 having an accumulation surface 30A is provided to face the voltage-applying roller 20, the accumulation surface 30A facing the voltage-applying roller 20. A metallic block 31 is provided to face the voltage-applying roller 20 to interpose the accumulation conveyor 30, and is connected to the high-voltage generator 21 to be negatively charged.

The accumulation conveyor 30 is a conductive material, for example, a belt-shaped member formed from aluminum or the like, or an unwoven fabric formed from a paper or a synthetic fiber that does not lower the conductivity of the metallic block 31. The accumulation conveyor 30 is unwound by an unwinding roller (not shown) and wound by a winding roller (not shown).

Two guide rollers 32 are arranged longitudinally in the flowing direction of the accumulation conveyor 30 of the metallic block 31.

A distance between the voltage-applying roller 20 and the accumulation surface 30A of the accumulation conveyor 31 is not particularly limited, and may be arbitrarily decided in accordance with a state of an accumulated fiber assembly so that a solvent is easily evaporated. An applied voltage may vary depending on a property of the solution and an amount of the accumulated fiber assembly. The higher the voltage, the more fiber is obtained. For example, the voltage may be set in a range of 60 to 78 kV.

A static electric field is formed between the voltage-applying roller and the metallic block which work as two electrodes. The eggshell membrane solution adhered on the voltage-applying roller is extracted in filaments toward the metallic block and accumulated on the accumulation surface. The distance between the electrodes may be set in a range of 100 to 140 mm, for example.

4. Producing Method of Fiber and Fiber Assembly

An exemplary embodiment of the producing method for the fiber and the fiber assembly will be described below. According to the exemplary embodiment, the electrospinning method (i.e., electrolytic spinning, electrostatic spinning) is employed as the fiber producing method using the electrospinning device shown in FIGS. 1 and 2.

After stocking the eggshell membrane solution in the solution immersion vessel 10, the accumulation conveyor 30 is driven. Since the metallic block 31 connected to the high-voltage generator 21 is provided near the accumulation conveyor 30, the charges are induced and accumulated on a surface of the solution when the high voltage is applied. Thus generated electrostatic attractive force acts against a surface tension of the eggshell membrane solution. When an electric field force exceeds a critical value, the electrostatic attractive force exceeds the surface tension so that jets of the charged solution are ejected. Since the ejected jets have a large surface area relative to a volume, the solvent is effectively evaporated and a charge density increases due to decrease of the volume. Accordingly, the jets become finer. Due to the jet ejection of the solution, the solution is autonomously pulled toward the metallic block 31 for spinning.

The spun fiber containing the eggshell membrane component is accumulated on the accumulation surface 30A of the accumulation conveyor 30. Since the accumulation conveyor 30 is wound in a predetermined direction, the accumulated fiber (fiber assembly) containing the eggshell membrane component has a constant thickness along the longitudinal direction of the conveyor.

For varying properties of the finally obtained fiber (fiber assembly), various conditions of the electrospinning device may vary. For example, the voltage may be set in the range of 60 to 78 kV as described above. The jets may not be generated when the voltage is too low and a spark may be generated when the voltage is too high. The distance between the electrodes may be set in the range of 100 to 140 mm. The solvent may not be sufficiently evaporated when the distance is too short and the jets may not be generated when the distance is too long. A speed of the accumulation conveyor 30 may be arbitrarily set in a range of 4 to 10 cm per minute. The solvent may not be sufficiently evaporated when the speed is too slow and accumulation variations may be caused due to decrease of a Metsuke (a weight per unit area) when the speed is too fast. A net Metsuke of the unwoven fabric that forms the accumulation conveyor 30 may be arbitrarily set in a range of 0.5 to 4.0 g per square meter by repeatedly accumulating the fiber under a condition that the accumulation variations are small. Under such condition, the fiber (fiber assembly) having a diameter in the range of 100 to 500 nm can be preferably produced.

The accumulated fiber assembly is exfoliated from the accumulation conveyor 30 by a particular device (not shown). Before or after the exfoliation, a conventional cross-linking process such as thermal cross-linking, ultraviolet cross-linking, radiation cross-linking, and glutaraldehyde cross-linking may be conducted.

5. Advantages of the Exemplary Embodiments

Thus, the following advantages can be attained according to the exemplary embodiments.

(1) The fiber assembly formed from the fiber has substantially the same properties of the natural eggshell membrane since the fiber itself contains the eggshell membrane component. Specifically, since the eggshell membrane component itself contributes to form the fiber, the inherent properties of the eggshell membrane can be retained differently from the case where the eggshell membrane component is formed in a film-shape or the case where the eggshell membrane component is simply adhered to a surface of a synthetic fiber or a natural fiber. For example, when the fiber assembly is used as the wound dressing, cell-producing action of amino acid, adherence to texture due to the network structure, appropriate moisture retention, air permeability and stypticity due to filter effect can be exhibited by imitating the network structure of the natural eggshell membrane.

(2) The fiber assembly may be preferably used as the wound dressing or a cosmetic sheet since the fiber assembly is excellent in adherence to skin tissue of a human body. Further, since a shape and an area of the fiber assembly are not limited, unfavorable features of the nature eggshell membrane that an extractable eggshell membrane varies in size depending on egg size and is not flattened in shape are eliminated.

(3) The fiber contains not only the eggshell membrane component, but also the polyphenols such as the catechins, thereby producing several effects such as antibacterial, antiviral, antioxidative, deodorant and antiallergic effects. Further, the fiber assembly excellent in water resistance without a particular cross-linking process can be obtained when the polyphenols form a complex with the eggshell membrane component.

(4) The surface area of the fiber assembly can be enlarged as long as producible as the fiber assembly and the stypticity due to the filter effect can be exhibited since the fiber diameter is between and including 0.01 and 3 μm. Thus, the properties of the normal eggshell membrane such as a wound dressing effect, air permeability and adherence to the skin tissue can be securely exhibited.

(5) The properties that the natural eggshell membrane is not given (for example, a high fiber strength) can be given to the fiber and the fiber assembly by blending the binder with the fiber.

(6) The electrospinning method (i.e., electrolytic spinning, electrostatic spinning) is employed as the fiber producing method according to the exemplary embodiments. Accordingly, the fiber assembly having a diameter which cannot be directly obtained from the eggshell membrane can be easily produced by controlling spinning conditions. Further, the eggshell membrane component is prevented from pyrolysis since the spinning can be performed at ordinary temperature in the electrospinning method. Also, environmental burdens are reduced since the spinning can be performed even when the solvent is water.

(7) The fiberization (spinning) can be easily performed since the fiber-spinning solution contains the above-described various polymers, whereby the fiber producing process including the control of the fiber diameter can be easily conducted. Features of the various polymers such as mechanical strength and heat resistance can be given to the finally obtained fiber.

Figure 3:
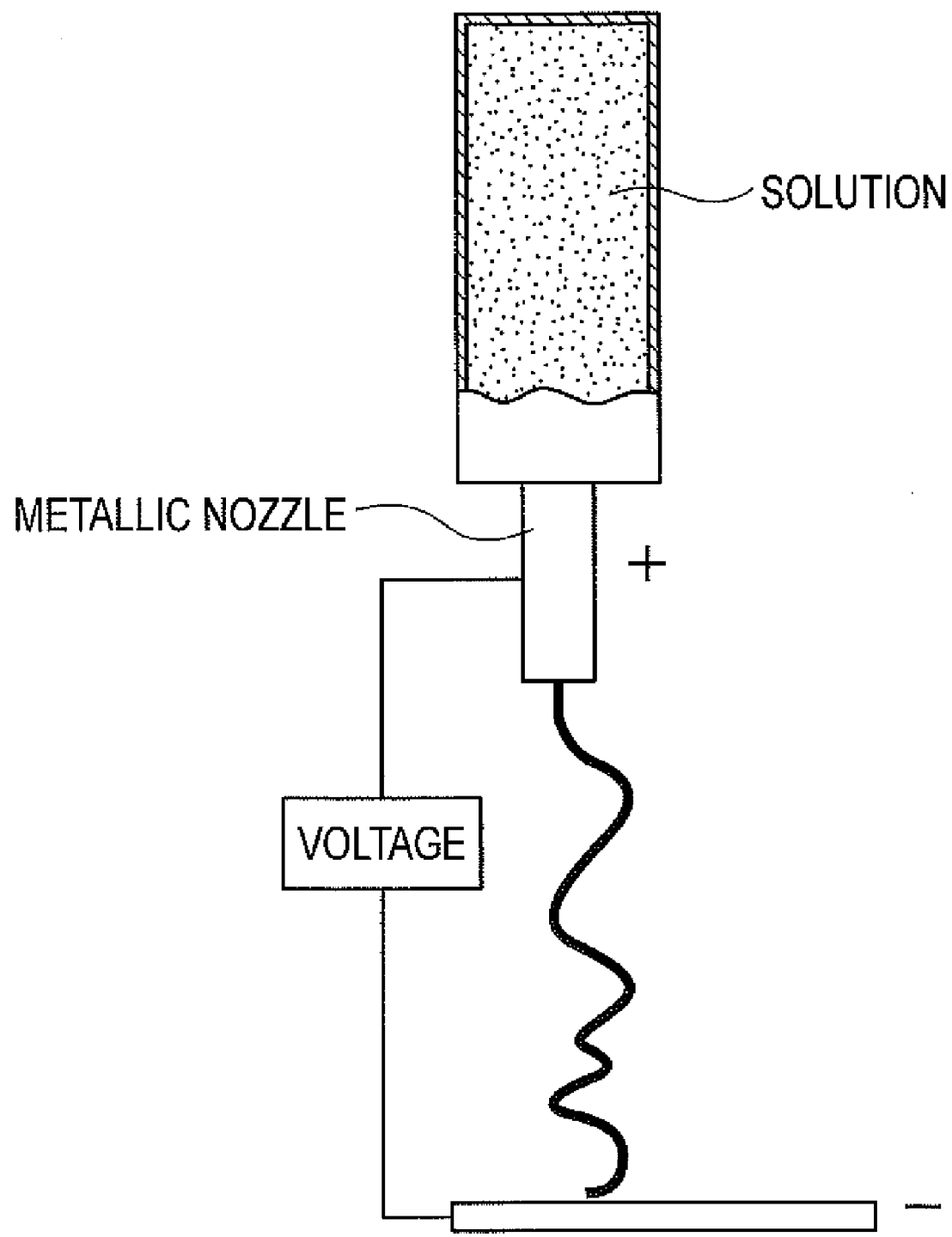
FIG. 3 is a schematic diagram showing a producing device (nozzle type) for a fiber producing method according to another exemplary embodiment of the present invention.
Figure 4A:
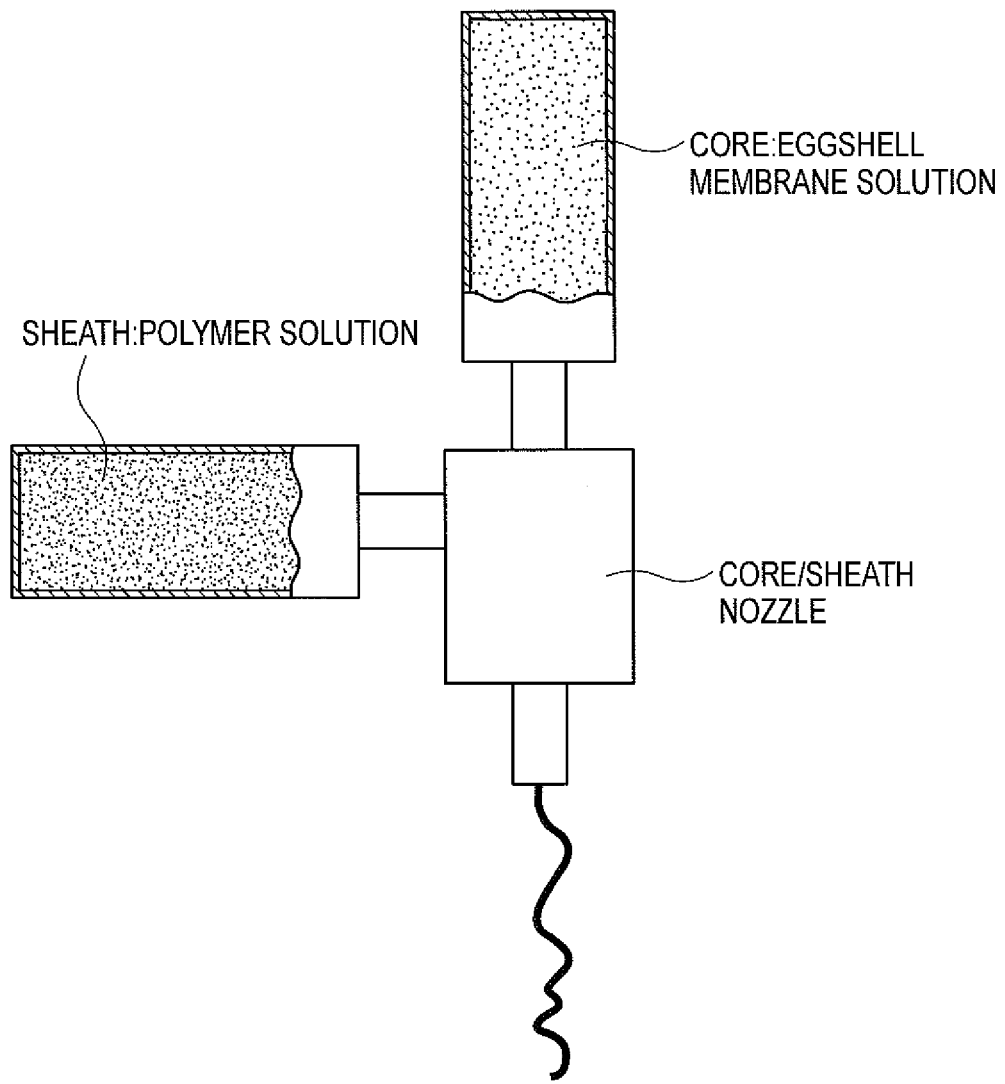
FIG. 4A is a schematic diagram showing a producing device (core/sheath nozzle type) for a fiber producing method according to still another exemplary embodiment of the present invention.
Figure 4B:
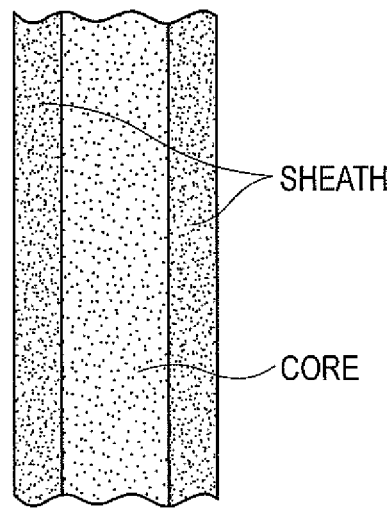
FIG. 4B is another schematic diagram showing the producing device (core/sheath nozzle type) for the fiber producing method according to the still another exemplary embodiment of the present invention.

(8) The fiber producing device according to the exemplary embodiments includes: the solution immersion vessel 10 filled with the eggshell membrane solution; the voltage-applying roller 20 provided in the solution immersion vessel 10; and the accumulation conveyor 30 on which the fiber-spinning is performed by the electrostatic attractive force generated via the voltage-applying roller 20 and the spun fiber is accumulated. The fiber-spinning method using a nozzle may be adopted as the electrospinning method as long as the object of the present invention is achieved. For example, a nozzle-type producing device (a fiber-spinning device) as shown in FIG. 3 is also preferable. Jets of a solution are ejected from a syringe to be accumulated as nanofibers on a collector by applying charges in a range of 5 to 30 kV to a nozzle portion of the fiber-spinning device. When a nozzle having a double-tube structure as shown in FIGS. 4A and 4B is used as the nozzle-type fiber-spinning device, nanofibers having a core/sheath structure are easily obtained. For example, even when the spinning using the electronspinning method is difficult to be performed for the eggshell membrane solution only, the fiber spinning can be performed to form a fiber having the core/sheath structure by using a polymer solution stocked in a sheath portion that is excellent in spinnability. Even when the core remains in the form of the solution, the fiberization is easily performed since the polymer solution stocked in the sheath portion is excellent in spinnability. Especially, the above-described device may be preferably used when the spinning using the electrospinning method is difficult to be performed under a condition that the solvent is not easily evaporated in the eggshell membrane solution only, and a concentration is lowered after dialysis. When the sheath portion is remained in the device having the core/sheath structure, several effects such as cell-producing action which are obtained by bringing out the eggshell membrane component may not be exhibited. Thus, the polymer in the sheath portion may be preferably removed after the core/sheath structure is formed.

(9) An insoluble material similar to the natural eggshell membrane can be obtained by conducting the cross-linking process for the spun fiber.

It should be understood that the present invention is not limited to the above-described embodiments, and includes modifications and improvements in the content of the present invention as long as an object of the present invention can be achieved.

For example, although the electrospinning method is employed to obtain the ultrafine fiber without degrading the eggshell membrane component according to the exemplary embodiments, other fiber spinning methods may be employed as long as an object of the present invention can be achieved.

Although the static electric field is formed between the voltage-applying roller 20 and the metallic block 31 which work as a pair of electrodes in the electrospinning device according to the exemplary embodiments, a plurality of static electric fields may be formed between a plurality of pairs of electrodes or in the solution immersion vessel. At this time, a plurality of voltage-applying rollers 20 may have different voltage values.

6. EXAMPLES

The advantages of the present invention will be more specifically described below by providing examples and comparisons. The present invention is not limited to the examples, and various modifications may be made without departing from the scope of the present invention.

Example 1

The eggshell membrane solution was prepared and the fiber (fiber assembly) containing the eggshell membrane was produced by employing the electrospinning method as described below.

Preparation of Eggshell Membrane

Polyvinyl alcohol (PV-217PVA, produced by Kuraray Co., Ltd.) having a saponification degree of 88 mol % after saponification and viscosity of 23 mPa·s at 20° C. for an aqueous solution of 4 mass % was used as the binder. A water-solubilized eggshell membrane (EMP-TF, produced by Idemitsu Technofine Co., Ltd.), ethanol, and a cross-linking agent in the form of glutaraldehyde were dissolved and mixed at a ratio (mass % ratio); the binder resin (PVA)/eggshell membrane/water/ethanol/glutaraldehyde=10/10/60/19/1.

Production of Fiber Assembly

The electrospinning was performed using the above-described eggshell membrane solution under a condition that the voltage was 70 kV, the distance between electrodes was 100 mm and the speed of the accumulation conveyor 30 was 4 cm per minute in the electrospinning device shown in FIGS. 1 and 2. The accumulation conveyor 30 was formed from polypropylene (PP) unwoven fabric at which the eggshell membrane solution was repeatedly accumulated.

Specifically, the charges were accumulated on the surface of the eggshell membrane solution. Then, the solution in filaments was jetted from the surface of the voltage-applying roller 20 when the charges increased over the surface tension of the solution. The jets of the solution were accumulated on the accumulation conveyor 30 while repeating evaporation of the solvent, increase of the charge density, and refinement of the filaceous solution. The net Metsuke of the fiber assembly was 1.8 g per square meter.

Further, the thermal cross-linking process was conducted for the fiber assembly for 30 minutes at 160° C. Finally, a fiber assembly having the eggshell membrane component of 50 mass % and the binder (PVA) of 50 mass % was obtained. FIGS. 5A and 5B show scanning electron micrographs of the fiber assembly. The fiber diameter was about 460 nm. It should be understood from the scanning electron micrographs that the fiber assembly according to the present invention has the network structure imitating the eggshell membrane.

Example 2

Preparation of Eggshell Membrane Solution A powder (E-SF, produced by Idemitsu Technofine Co., Ltd.) obtained by mechanically pulverizing the eggshell membrane was mixed into β-thiopropionate of 10 mol/l at a concentration of 5 mass %, and agitated at 80° C. for two days to form a solution of the eggshell membrane.

Production of Fiber Assembly

Figure 6:
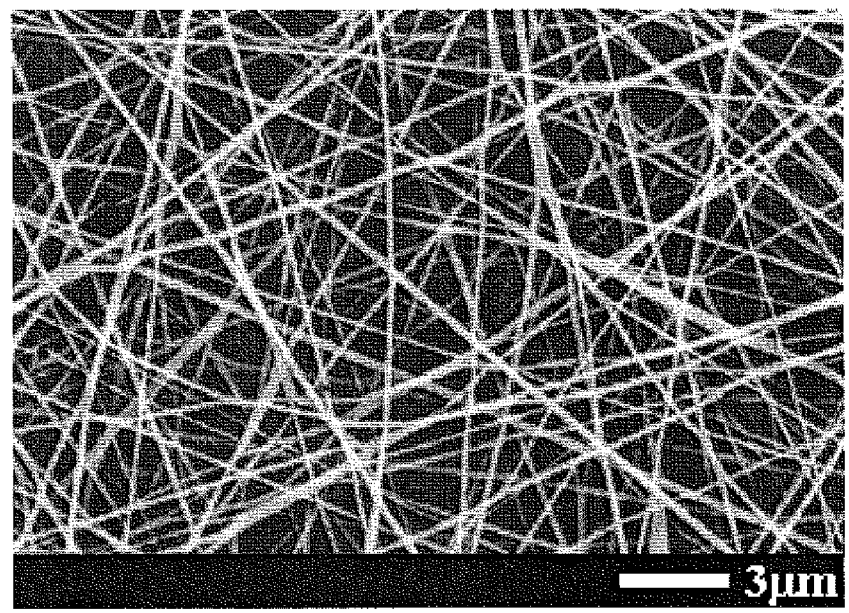
FIG. 6 shows a scanning electron micrograph of a fiber assembly after spinning according to an example 2.

The solution obtained as described above was used for forming the core and a PVA (PVA-217, produced by Kuraray Co., Ltd.) aqueous solution of 10 mass % was used for forming the sheath. The spinning was performed using the electrospinning device having the core/sheath nozzle as shown in FIGS. 4A and 4B under a condition that a supply ratio of the above-described solution: PVA aqueous solution was 1:3 to obtain a fiber assembly having a diameter of about 110 nm. FIG. 6 shows a scanning electron micrograph of the above-described fiber assembly. It should be understood from the scanning electron micrograph that the fiber assembly according to the present invention has the network structure imitating the eggshell membrane.

Example 3

Preparation of Eggshell Membrane 2 g of the powder (E-SF, produced by Idemitsu Technofine Co., Ltd.) obtained by mechanically pulverizing the eggshell membrane was mixed with 6 g of 15 mol/l urea, 0.5 g of sodium lauryl sulfate, 20 g of mercaptoethanol and 6 g of distilled water, and agitated at 80° C. for two days to form a solution of the eggshell membrane. The solution is dialyzed for one day to obtain an eggshell membrane solution.

Production of Fiber Assembly

Figure 7:
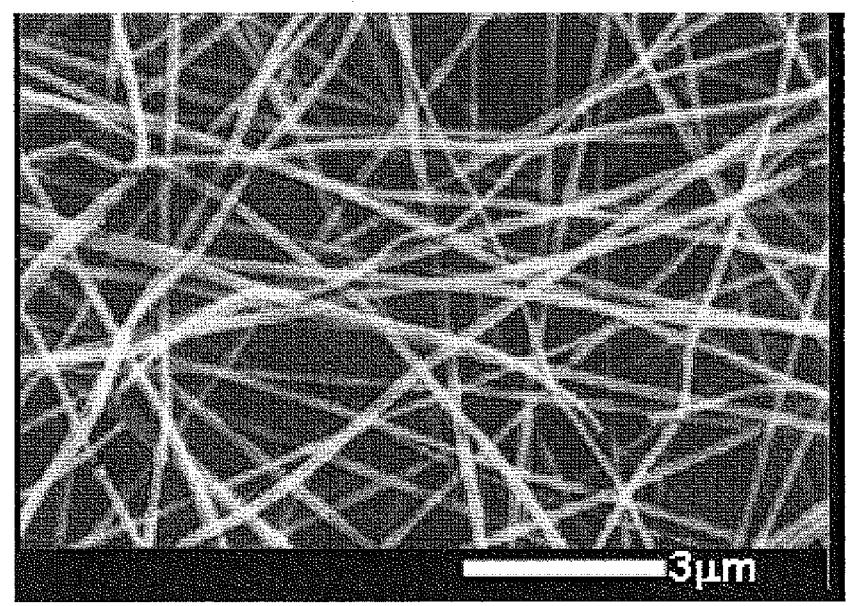
FIG. 7 shows a scanning electron micrograph of a fiber assembly after spinning according to an example 3.
Figure 8:
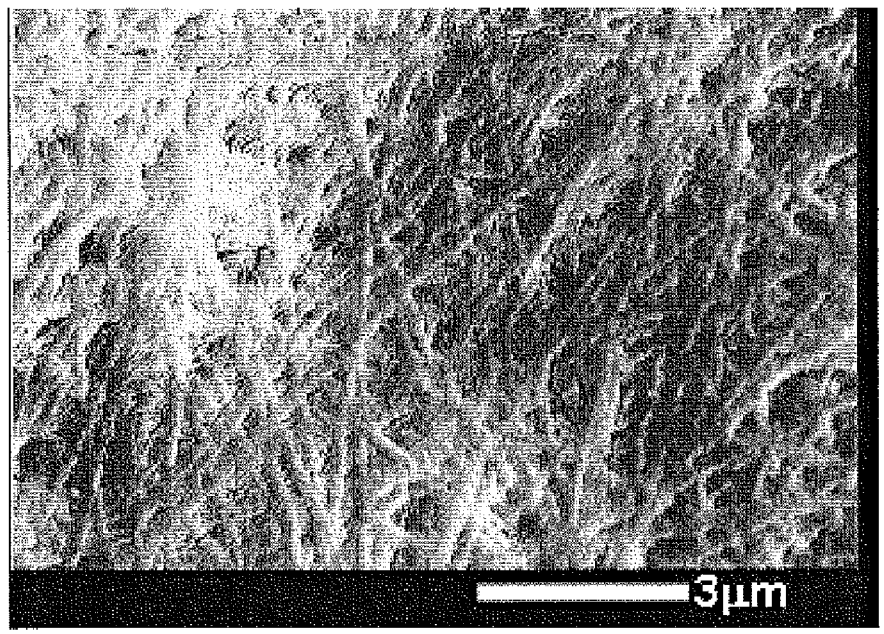
FIG. 8 shows another scanning electron micrograph of the fiber assembly (after oxidation and cross-linking) after spinning according to the example 3.

The eggshell membrane solution obtained as described above was used for forming the core and a PEO (polyethylene oxide, Mw=900000, produced by Acros Organics) aqueous solution of 7 mass % was used for forming the sheath. The spinning was performed using the electrospinning device having the core/sheath nozzle as shown in FIGS. 4A and 4B under a condition that a supply ratio of the eggshell membrane solution: PEA aqueous solution was 1:3 to obtain a fiber assembly having a diameter of about 220 nm. The fiber assembly was dipped in a methanol solution containing 2 mass % of iodine for two hours to conduct the oxidation and cross-linking process. Then, the fiber assembly was dipped in water for one day to be washed with water so that a fiber assembly having a fiber diameter of about 390 nm and containing the eggshell membrane component was obtained. FIG. 7 shows a scanning electron micrograph of the fiber assembly before the oxidation and cross-linking process and FIG. 8 shows another scanning electron micrograph after the oxidation and cross-linking process. It should be understood from the scanning electron micrographs that the fiber assembly according to the present invention has the network structure imitating the eggshell membrane. Further, due to the oxidation and cross-linking process, an S—S bond that was dissociated when the eggshell membrane was dissolved was recombined and reconfigured in the insoluble material similar to the natural eggshell membrane.

Example 4

Preparation of Eggshell Membrane Solution

By using a polyvinyl alcohol (PVA-217, produced by Kuraray Co., Ltd.) aqueous solution of 40 mass % having a saponification degree of 88 mol % after saponification and viscosity of 23 mPa·s at 20° C. as the binder, the water-solubilized eggshell membrane (EMP-TF, produced by Idemitsu Technofine Co., Ltd.), and ethanol were dissolved and mixed to obtain the eggshell membrane solution at a ratio (mass % ratio); PVA/eggshell membrane/water/ethanol=8/8/74/10.

Production of Fiber Assembly

Figure 9:
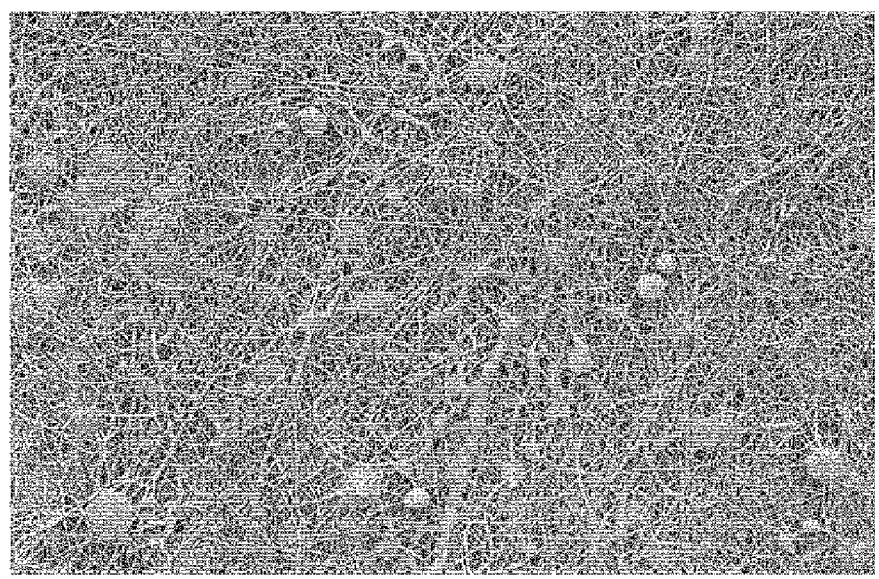
FIG. 9 shows a scanning electron micrograph of a fiber assembly after spinning according to an example 4.

The spinning was performed using the eggshell membrane solution obtained as described above in the electrospinning device as shown in FIG. 1 to obtain a fiber assembly. After the fiber assembly was dipped in the aqueous solution for 12 hours for an insolubilization process (chemical cross-linking) under a condition that glutaraldehyde/sodium sulfate/sulfuric acid was 0.06/0.96/0.4 (mol/l), the fiber assembly was washed with water and dried at ambient temperature so that the fiber assembly having a fiber diameter of about 330 nm and containing the eggshell membrane component was obtained. FIG. 9 shows a scanning electron micrograph of the above-described fiber assembly. It should be understood from the scanning electron micrograph that the fiber assembly according to the present invention has the network structure imitating the eggshell membrane.

Example 5

Preparation of Eggshell Membrane Solution

The PEO (Mw=900000, produced by Acros Organics) as the binder and the water-solubilized eggshell membrane (EMP-TF, produced by Idemitsu Technofine Co., Ltd.) were mixed and dissolved in water to obtain an eggshell membrane solution at a ratio (mass % ratio); PEO/eggshell membrane/water=2/18/80.

Production of Fiber Assembly

Figure 10:
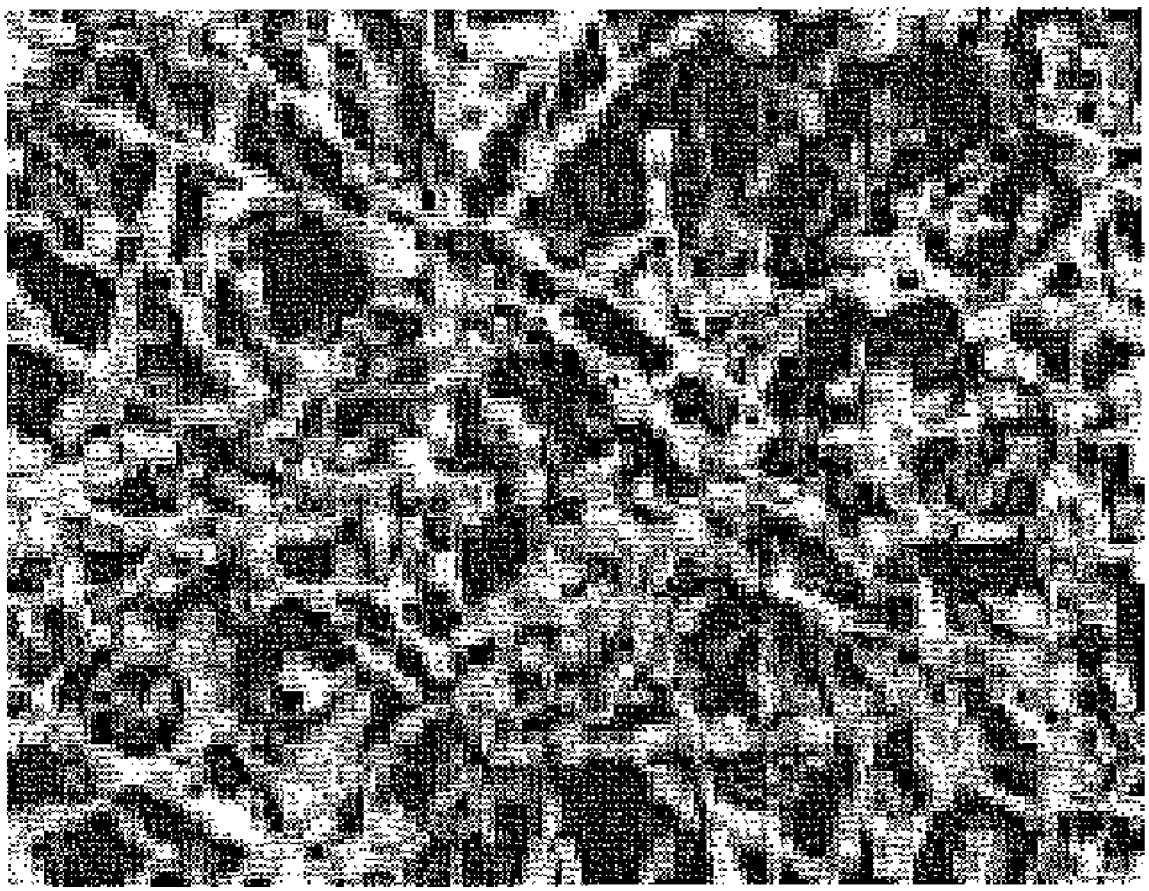
FIG. 10 shows a scanning electron micrograph of a fiber assembly after spinning according to an example 5.

The spinning was performed using the eggshell membrane solution obtained as described above in the electrospinning device shown in FIG. 1 to obtain a fiber assembly. After the fiber assembly was dipped in an ethanol solution containing catechin (polyphenon 70A, produced by Mitsui Norin Co., Ltd.) of 10 mass % for 72 hours to conduct the insolubilization process, the fiber assembly was washed with water and dried at ambient temperature so that a fiber assembly having a fiber diameter of about 300 nm and containing the eggshell membrane component and catechin was obtained. FIG. 10 shows a scanning electron micrograph of the above-described fiber assembly. It should be understood from the scanning electron micrograph that the fiber assembly according to the present invention has the network structure imitating the eggshell membrane.

Comparison 1

After the eggshell membrane solution obtained in Example 1 was put on a glass petri dish and dried, the eggshell membrane solution was washed with methanol to obtain the film-shaped eggshell membrane. However, the above-described eggshell membrane did not possess sufficient air permeability due to lack of the network structure of the natural eggshell membrane.

Comparison 2

After the eggshell membrane power (E-SF, produced by Idemitsu Technofine Co., Ltd.) was blended with the binder in the form of an acrylic-silicone resin fiber treatment agent (light epoch S-60NFE, produced by Kyoeisha Chemical Co., Ltd.) at a ratio (mass % ratio); E-SF/light epoch S-60NFE/water=18/40/42, the solution was agitated and dispersed for immersion and squeezing to have a 100% pickup ratio relative to a mass of a fiber. However, the powder was too clingy to produce the fiber.

Comparison 3

After the water-solubilized eggshell membrane (EMP-TF, produced by Idemitsu Technofine Co., Ltd.) was blended with the binder in the form of the acrylic-silicone resin fiber treatment agent (light epoch S-60NFE, produced by Kyoeisha Chemical Co., Ltd.) at a ratio (mass % ratio); EMP-TF/light epoch S-60NFE/water=18/40/42, the solution was agitated and dissolved for immersion and squeezing to have the 100% pickup ratio relative to a mass of a fiber. However, the eggshell membrane was too agglutinated to produce the fiber.

The priority applications respectively numbered as JP2007-197274 and JP20 08-108740 upon which this patent application is based are hereby incorporated by reference.

What is claimed is:

1. A fiber containing an eggshell membrane component therein.

2. The fiber according to claim 1, further containing polyphenols.

3. The fiber according to claim 2, wherein the polyphenols contain catechins.

4. The fiber according to claim 3, wherein the catechins contain at least one of epicatechin, epicatechin gallate, epigallocatechin, epigallocatechin gallate and attributes thereof.

5. The fiber according to claim 1, further containing a polymer molecule.

6. The fiber according to claim 1, wherein a content of the eggshell membrane component is 20 mass % or more.

7. The fiber according to claim 1, wherein the diameter of the fiber is 0.01 µm or more and 3 µm.

8. A fiber assembly produced by assembling the fiber according to claim 1.

9. A method for producing the fiber according to claim 1, wherein a spinning is performed using a solution containing an eggshell membrane component by employing an electro-spinning method.

10. The method for producing the fiber according to claim 9, wherein the solution containing the eggshell membrane component contains polymer molecule.

11. The method for producing the fiber according to claim 9, wherein a fiber having a core/sheath structure is spun by employing the electrospinning method.

12. The method for producing the fiber according to claim 11, wherein a solution containing the eggshell membrane component is used for forming a core portion, and a polymer solution is used for forming a sheath portion.

13. The method for producing the fiber according to claim 11, wherein the sheath portion is removed after the core/sheath structure is formed by spinning.

14. The method for producing the fiber according to claim 9, wherein a cross-linking process is conducted for the spun fiber.

15. The fiber according to claim 7, wherein the diameter of the fiber is from 0.1 µm to 1.8 µm.

16. The fiber according to claim 5, wherein said polymer is polyurethane, silicone, polyvinylidene fluoride, polyacrylonitrile, polymethyl methacrylate, polyvinyl chloride, polyvinylidene chloride, polyethylene, polypropylene, nylon, polyvinyl alcohol, cellulose, polyvinyl acetate, polyethylene oxide, polyethylene imide, polyaniline, polyethylene sulfide, polystyrene, polybutadiene, polyethylene terephthalate, polylactic resin, polyglutamic acid, hyaluronic acid, starch, casein, collagen, nucleic acid, catechin, gelatin, sericin, fibroin, chitin, chitosan, organosilica or organotitanium.

17. The fiber according to claim 6, wherein the content of the eggshell membrane component is 50 mass % or more.

18. The fiber of claim 1, further comprising a polymer sheath spun from a solution.

19. A fiber blend comprising an eggshell membrane component and a polymer molecule.

* * * * *

UNITED STATES PATENT AND TRADEMARK OFFICE
CERTIFICATE OF CORRECTION

PATENT NO. : 7,767,297 B2  
APPLICATION NO. : 12/181560  
DATED : August 3, 2010  
INVENTOR(S) : Tajima et al.

It is certified that error appears in the above-identified patent and that said Letters Patent is hereby corrected as shown below:

Column 12, line 1 reads "The fiber according to claim 1, wherein a content of the" should read -- The fiber according to claim 1, wherein the content of the --

Column 12, line 4 reads "the fiber is 0.01 µm or more and 3µm." should read -- the fiber is 0.01 µm to 3µm. --

Signed and Sealed this

Ninth Day of November, 2010

David J. Kappos  
*Director of the United States Patent and Trademark Office*